United States Patent [19]

Wierzbicki et al.

[11] Patent Number: 5,703,074
[45] Date of Patent: Dec. 30, 1997

[54] THIOPHENE COMPOUNDS

[75] Inventors: Michel Wierzbicki, L'Etang La Ville; Frédéric Sauveur, Argenteuil; Marie-Francoise Boussard, Mareil sur Mauldre; Jacqueline Bonnet, Paris; Massimo Sabatini, Garges, all of France

[73] Assignee: Adir Et Compagnie, Courbevvoie, France

[21] Appl. No.: 771,035

[22] Filed: Dec. 20, 1996

[30] Foreign Application Priority Data

Dec. 21, 1995 [FR] France .................... 95 15224

[51] Int. Cl.⁶ .................... C07D 413/06; A61K 31/535
[52] U.S. Cl. .................... 514/231.5; 544/146; 549/74; 514/430
[58] Field of Search ................. 544/146; 549/74; 514/231.5

[56] References Cited

U.S. PATENT DOCUMENTS 5,061,704  10/1991  Wierzbicki et al. .................... 544/146

Primary Examiner—Robert W. Ramsuer
Attorney, Agent, or Firm—The firm of Gordon W. Hueschen

[57] ABSTRACT

Thiophene compounds of formula:

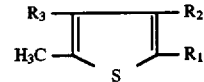

wherein $R_1$, $R_2$ and $R_3$ are as defined in the description, and salts thereof with appropriate acids.

Those compounds and their physiologically tolerable salts can be used as medicaments in the treatment of pathologies characterized by a loss of bone tissue.

4 Claims, No Drawings

THIOPHENE COMPOUNDS

The present invention relates to new thiophene compounds, and pharmaceutical compositions containing them.

It relates more especially to thiophene compounds of formula I:

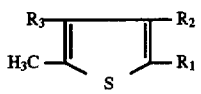
(I)

wherein:
one of $R_1$, $R_2$ and $R_3$ represents the radical of formula

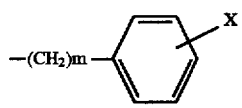

wherein:
m represents an integer of from 2 to 6 inclusive and

X represents a hydrogen atom, an alkyl or alkoxy radical each having from 1 to 5 carbon atoms in straight or branched chain, or a dialkylamino radical in which each alkyl group contains from 1 to 5 carbon atoms, one of $R_1$, $R_2$ and $R_3$ represents the radical of formula

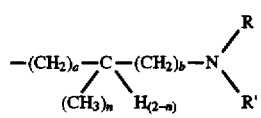

wherein:
n represents 0, 1 or 2;
a represents 2 or 3 and
b represents 1 or 2 such that a+b=4, and
R and R', which are identical or different, each represents a hydrogen atom or an alkyl radical having from 1 to 5 carbon atoms in straight or branched chain, or R and R' form together with the nitrogen atom to which they are bonded a five-membered or six-membered heterocyclic radical optionally containing an oxygen atom or a second nitrogen atom, which nitrogen atom may itself be substituted by an alkyl radical containing from 1 to 5 carbon atoms in straight or branched chain or by an arylalkyl radical in which the alkyl group contains from 1 to 5 carbon atoms and the aryl group is optionally mono- or poly-substituted by a halogen atom or by an alkyl or alkoxy radical each having from 1 to 5 carbon atoms, and one of $R_1$, $R_2$ and $R_3$ represents a hydrogen atom or a methyl radical.

The closest prior art to the present invention is illustrated especially by the patent specification EP-A-429 370 which relates to thiophene compounds of formula:

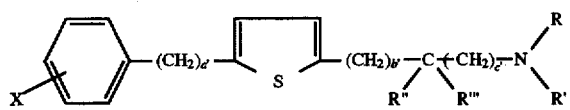

which have a bone anti-resorbent activity, but nowhere suggests the compounds of the present invention.

The compounds of formula I have been prepared according to a process which is characterized in that:

the acid of formula II:

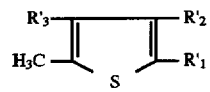
(II)

wherein:
one of $R'_1$, $R'_2$ and $R'_3$ represents the radical of formula

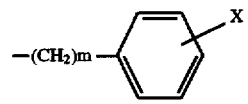

wherein m and X are as defined above;
one of $R'_1$, $R'_2$ and $R'_3$ represents the radical of formula

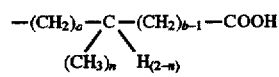

wherein n, a and b are as defined above, and
one of $R'_1$, $R'_2$ and $R'_3$ represents a hydrogen atom or a methyl radical is converted into the corresponding amide of formula III:

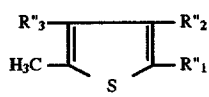
(III)

wherein:
one of $R''_1$, $R''_2$ and $R''_3$ represents the radical of formula

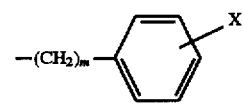

wherein m and X are as defined above,
one of $R''_1$, $R''_2$ and $R''_3$ represents the radical of formula

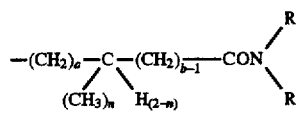

wherein n, a, b, R and R' are as defined above and
one of $R''_1$, $R''_2$ and $R''_3$ represents a hydrogen atom or a methyl radical;

and the amide of formula III is reduced to obtain the corresponding compounds of formula I.

The conversion of the acid of formula II into the amide of formula III is carried out according to conventional methods known from the literature, such as, for example, the conversion of the acid into the corresponding acid chloride which is used to acylate the amine of formula:

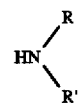

wherein R and R' are as defined above.

The acylation is carried out in the presence of an acceptor for the hydrochloric acid formed during the course of the reaction; that acceptor may be, for example, an excess of the amine used for the reaction.

The reduction of the amide of formula III is carried out especially suitably by means of $LiAlH_4$ at reflux in a suitable solvent, such as, for example, ether.

The starting acids of formula III were prepared from known starting materials according to known processes as described hereinafter.

The compounds of formula I yield salts with physiologically tolerable acids, which salts, as such, are included in the present invention.

The compounds of the present invention exhibit pharmacological and therapeutic properties that are valuable especially with respect to bone metabolism while at the same time being non-toxic, enabling them to be used in pathologies characterized by a loss of bone tissue, such as osteoporosis, Paget's disease, parodontitis and rheumatoid polyarthritis.

The present invention relates also to pharmaceutical compositions containing as active ingredient a compound of the general formula I or a physiologically tolerable salt thereof, mixed with or associated with an appropriate pharmaceutical excipient, such as, for example, glucose, lactose, starch, talc, ethyl cellulose, magnesium stearate or cocoa butter.

The pharmaceutical compositions so obtained are generally presented in dosage form and may contain from 0.1 to 10 mg of active ingredient.

They may be in the form of tablets, dragées, gelatin capsules, suppositories, or injectable or drinkable solutions and, depending on the case in question, may be administered by the oral, rectal or parenteral route.

The dosage varies especially in accordance with the age and weight of the patient, the administration route, the nature of the disorder and associated treatments, and ranges from 0.2 to 20 mg of active ingredient once or twice per day.

The following Examples illustrate the present invention. The melting points are determined using a Kofler hot plate, unless specified otherwise.

I. Synthesis of the starting materials of formula II

A) 2-methyl-3-(4-carboxy-3,3-dimethylbutyl)-5-(3-p-methylphenylpropyl)thiophene, (A1) and 2-methyl-4-(4-carboxy-3,3-dimethylbutyl)-5-(3-p-methylphenylpropyl)thiophene, (A2):

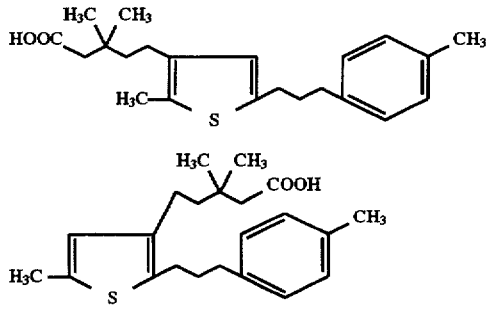

(A1)

(A2)

Step 1: 2-methyl-5-(p-methylphenylpropionyl)thiophene

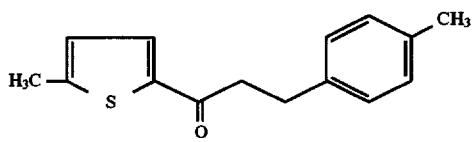

160.65 g (1.35 mol) of thionyl chloride are placed in a 1 liter three-necked flask fitted with a mechanical stirrer and a condenser. 164.2 g (0.9 mol) of p-methylphenylpropionic acid are added little by little thereto at room temperature. After 4 hours, the reaction is terminated by heating at 60° C. for 1 hour. Excess $SOCl_2$ is removed by distillation/n vacuo.

In that manner 164.5 g of p-methylphenylpropionic acid chloride are obtained.

91 g (0.99 mol) of 2-methylthiophene, 1.4 l of dichloromethane and the previously prepared acid chloride are placed in a 3 liter three-necked flask fitted with a $CaCl_2$ guard, a mechanical stirrer, a thermometer and a dropping funnel.

The reaction mixture is brought to 5° C. with an ice bath, and then 281.3 g (1.08 mol) of $SnCl_4$ are added in the course of 40 minutes during which the temperature is maintained below 5° C. Subsequently, after 12 hours at room temperature, the mixture is hydrolysed with a mixture of water/ice/concentrated HCl (1 liter/500 g/170 ml). The organic phase is separated and the aqueous phase is extracted with $CH_2Cl_2$.

The combined organic phases are washed with dilute HCl and then with $H_2O$, treated with $MgSO_4$ and carbon black and then concentrated. The residue, recrystallised from cyclohexane, yields 173 g of the expected product in the form of a white solid melting at 52° C. Yield: 79%.

Step 2: 2-methyl-5-(p-methylphenylpropyl)thiophene

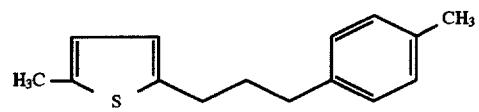

90 g (0.369 mol) of 2-methyl-5-(p-methylphenylpropionyl)thiophene and 965 ml of triethylene glycol are introduced into a 3 liter three-necked flask fitted with a mechanical stirrer, a condenser and a thermometer.

The reaction mixture is warmed to 55° C. and 64.30 g (1.27 mol) of hydrazine hydrate are added thereto in one go. The temperature is brought to 90° C. and 63.2 g (1.127 mol) of potassium hydroxide pellets are added to the mixture. The reaction mixture is brought to a vigorous reflux and the water is distilled off. The temperature rises to 220° C. where it is maintained for 45 minutes.

After cooling to 50° C., 900 ml of water and 155 ml of concentrated HCl are added. The mixture is extracted with ether. The organic phases are washed in succession with dilute HCl, $H_2O$, dilute NaOH and $H_2O$ and then dried over $MgSO_4$, rendered colourless with carbon black and concentrated.

The oil obtained is distilled in vacuo (13.33 Pa). 77.5 g of the expected product are obtained in the form of a colourless oil, b.p./$_{13.33 Pa}$=110°–115° C. Yield: 91%.

Step 3: 2-methyl-3-(4-ethoxycarbonyl-3,3-dimethylbutanoyl)-5-(p-methylphenylpropyl)thiophene (A'1) and 2-methyl-4-(4-ethoxycarbonyl-3,3-dimethylbutanoyl)-5-(p-methylphenylpropyl)thiophene (A'2)

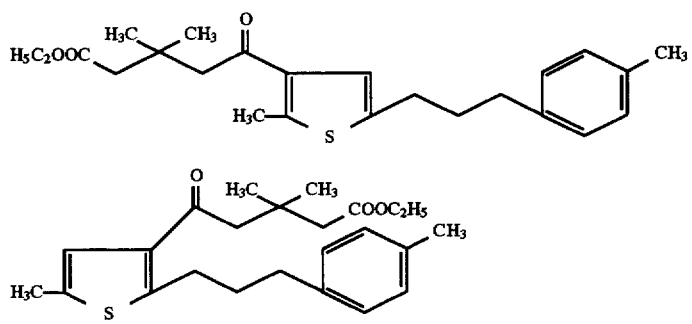

(A'₁)

(A'₂)

15 g (0.0651 mol) of 2-methyl-5-(p-methylphenylpropyl) thiophene, 10.2 g (0.0716 mol) of 3,3-dimethylglutaric anhydride and 115 ml of nitrobenzene are placed in a 250 ml three-necked flask fitted with a mechanical stirrer and a thermometer. The mixture is brought to 0° C. with an ice bath and 13 g (0.0976 mol) of aluminum chloride are added in portions. After 1 hour at 0° C. and 2 hours at room temperature, the mixture is hydrolysed with a mixture of water/ice/concentrated HCl (90 g/90 g/18 ml) and then decanted. The nitrobenzene is removed by stripping with steam and the residue is extracted with $CH_2Cl_2$. The organic phase is washed with dilute HCl and then $H_2O$, dried over $MgSO_4$, rendered colourless with carbon black and concentrated. The oil obtained is constituted by a mixture of which 51% is 2-methyl-3-(4-carboxy-3,3-dimethylbutanoyl)-5-(p-methylphenylpropyl)thiophene and 49% is 2-methyl-4-(4-carboxy-3,3-dimethylbutanoyl)-5-(p-methylphenylpropyl) thiophene.

The mixture of crude acids is esterified by the action of ethanol in the presence of p-toluenesulphonic acid. After customary treatment, the mixture of esters is subjected to chromatography on silica (eluant: $CH_2Cl_2$). The relevant fractions are combined and concentrated yielding:

10.17 g of a colourless oil identical to the ester of formula A'₁ (yield: 39%);

8 g of a colourless oil constituted by a mixture of the esters A'₁ and A'₂; and 3.9 g of a colourless oil identical to the ester of formula A'₂ (yield: 15%).

Step 4: Title products (A₁) and (A₂)

7.7 g (0.0192 mol) of 2-methyl-3-(4-ethoxycarbonyl)-3, 3-dimethylbutanoyl)-5-(p-methylphenylpropyl)thiophene (A'₁) and 80 ml of triethylene glycol are placed in a 250 ml three-necked flask fitted with a mechanical stirrer, a condenser and a thermometer. The reaction mixture is brought to 60° C. and 3.35 g (0.067 mol) of hydrazine hydrate are added thereto in one go. The reaction is brought to a vigorous reflux. The water is distilled off and the temperature is brought to 210° C. for 35 mutes. After cooling, the mixture is hydrolysed with 120 ml of water and 25 ml of concentrated HCl, and then decanted. The aqueous phase is extracted with $CH_2Cl_2$. The organic phases are washed with dilute HCl and then $H_2O$, dried over $MgSO_4$, rendered colourless with carbon black and concentrated.

9.3 g of 2-methyl-3-(4-carboxy-3,3-dimethylbutyl)-5-(3-p-methylphenylpropyl)thiophene are obtained in the form of a pale yellow oil, yield: 91%.

By proceeding in the same manner, but using the ester of formula A'2 instead of the ester of formula A'1, 2-methyl-4-(4-carboxy-3,3-dimethylbutyl)-5-(3-p-methylphenylpropyl)thiophene was obtained.

B) 2,3-dimethyl-4-(3-p-methylphenylpropyl)-5-(4-carboxy-3,3-dimethylbutyl)thiophene Step 1: 2,3-dimethyl-5-(4-carboxy-3,3-dimethylbutanoyl) thiophene

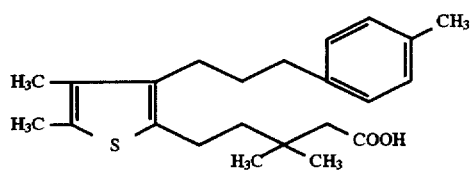

40 g (0.355 mol) of 2,3-dimethylthiophene, 630 ml of nitrobenzene and 55.5 g (0.390 mol) of 2,3-dimethylglutaric anhydride are introduced into a 2 liter three-necked flask fitted with a mechanical stirrer. The mixture is brought to 0° C. and 71 g (0.532 mol) of aluminum chloride are added in portions while maintaining the temperature below 5° C. After 10 hours' stirring at room temperature, the mixture is hydrolysed with water/ice/concentrated HCl (500 g/500 g/170 ml) for 15 minutes. The nitrobenzene is then stripped off with steam and the residue is extracted 3 times with 100 ml of $CH_2Cl_2$ each time. The combined organic phases are washed with dilute HCl and then with $H_2O$, dried over $MgSO_4$, rendered colourless with carbon black and concentrated to yield 73.4 g of 2,3-dimethyl-5-(4-carboxy-3,3-dimethylbutanoyl)thiophene in the form of a pale yellow oil, yield: 81%.

Step 2: 2,3-dimethyl-5-(4-carboxy-3,3-dimethylbutyl) thiophene 72.9 g (0.29 mol) of 2,3-dimethyl-5-(4-carboxy-3,3-dimethylbutanoyl)thiophene and 580 ml of triethylene glycol are introduced into a 3 liter three-necked flask fitted with a stirrer, a condenser and a thermometer. After having warmed the mixture to about 40° C., 50.03 g (1 mol) of hydrazine monohydrate are added thereto in one go. The reaction mixture is then heated to 90° C. and 49.2 g (0.88 mol) of potassium hydroxide pellets are added thereto. The whole is heated to a vigorous reflux over 30 minutes (145° C.); the water is distilled off; the temperature rises to 200° C. where it is maintained for 1 hour.

After cooling to 50° C., 1.4 l of water and then 100 ml of concentrated HCl are added. The aqueous phase is extracted with ether; the ethereal phase is washed with dilute HCl, H₂O and then treated with MgSO₄ and carbon black. After concentration, the residue is crystallised in petroleum ether, filtered, suctioned off and dried. 49 g of 2,3-dimethyl-5-(4-carboxy-3,3-dimethylbutyl)thiophene are obtained in the form of a white solid, yield: 60%.

Step 3: 2,3-dimethyl-5-(4-ethoxycarbonyl-3,3-dimethylbutyl)thiophene

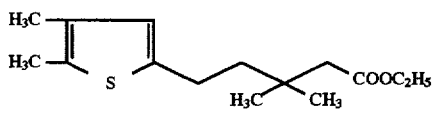

30 g (0.125 mol) of 2,3-dimethyl-5-(4-carboxy-3,3-dimethyl)butylthiophene, 60 ml of dimethylformamide and 20.73 g (0.15 mol) of potassium carbonate are introduced into a 500 ml three-necked flask fitted with a mechanical stirrer, a condenser and a thermometer. After having warmed the mixture to about 40° C., 21.45 g (0.137 mol) of methyl iodide are added thereto in the course of 30 minutes. The reaction mixture is maintained at 80° C. for 10 hours and then concentrated in vacuo and taken up in 250 ml of anhydrous ether. The potassium iodide is removed by filtration. The ethereal phase is washed with water, dried over MgSO4, rendered colourless with carbon black and concentrated. 32.96 g of 2,3-dimethyl-5-(4-ethoxycarbonyl-3,3-dimethylbutyl)thiophene are obtained in the form of a yellow oil, yield: 98%.

Step 4: 2,3-dimethyl-4-(3-p-methylphenylpropionyl)-5-(4-ethoxycarbonyl-3,3-dimethylbutyl)thiophene

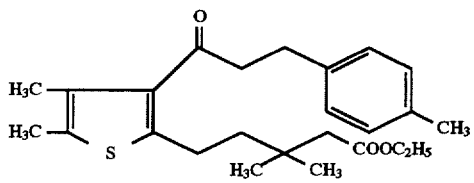

15.3 g (0.056 mol) of 2,3-dimethyl-5-(4-ethoxycarbonyl-3,3-dimethylbutyl)thiophene, the acid chloride prepared from 9.2 g (0.056 mol) of p-methylphenylpropionic acid and 6.1 ml (0.084 mol) of SOCl₂, and 90 ml of CH₂Cl₂ are introduced into a 250 ml three-necked flask. The reaction mixture is brought to 0° C. and then, in the course of 25 minutes, 8 ml (0.0672 mol) of SnCl₄ are added dropwise while maintaining the temperature below 5° C.

After 10 hours' stirring, the reaction mixture is hydrolysed with water/ice/concentrated HCl (90 g/90 g/11 ml) and extracted 3 times with 100 ml of CH₂C₁₂ each time.

The organic phases are washed with water and with sodium hydrogen carbonate, dried over MgSO₄ and rendered colourless with carbon black. After removal of the solvent by distillation, 21.74 g of the expected product are recovered in the form of a pale yellow oil (yield 94%), a sample of which is purified by chromatography on silica (eluant:cyclohexane/CH₂Cl₂, 80/20) to yield an analytically pure sample.

Step 5: Title product 10.5 g (0.025 mol) of the product obtained in Step 4 are dissolved in 50 ml of triethylene glycol in a 500 ml three-necked flask. The solution is heated to 80° C. and then 4.36 g (0.0863 mol) of hydrazine hydrate are added thereto. The temperature is then maintained at 95° C., and 4.29 g (0.0765 mol) of potassium hydroxide are subsequently added to the mixture. After 15 minutes' reflux (≈130° C.), the water formed is distilled off. When the temperature reaches 230° C., the reaction mixture is cooled to 20° C., hydrolysed with 125 ml of water, acidified with 90 ml of concentrated HCl and extracted 4 times with 25 ml of ethyl ether each time. The organic phases are washed with dilute HCl then H₂O, dried over MgSO₄ and rendered colourless with carbon black. The concentrated residue is chromatographed on silica (eluant: CH₂Cl₂/CH₃COOC₂H₅, 98/2). After concentration, 6.2 g of 2,3-dimethyl-4-(3-p-methylphenylpropyl)-5-(4-carboxy-3,3-dimethylbutyl) thiophene are obtained in the form of a colourless oil, yield: 70%.

C) 2-methyl-3-(3-p-methylphenylpropyl)-5-(4-carboxy-3,3-dimethylbutyl)thiophene and 2-methyl-4-(3-p-methylphenylpropyl)-5-(4-carboxy-3,3-dimethylbutyl) thiophene.

These two compounds were prepared according to the method described in paragraph B), starting from 2-methylthiophene and following separation of the intermediate esters of formulae A"₁ and A"₂.

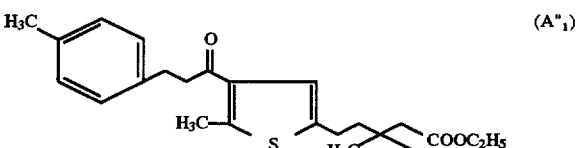

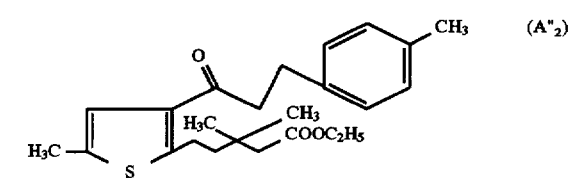

D) 2,5-dimethyl-3-(3-phenylpropyl)-4-(4-carboxy-3,3-dimethylbutyl)thiophene

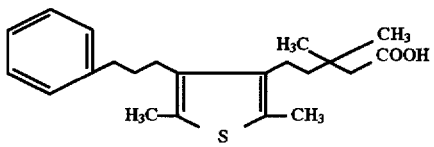

Step 1: 2,5-dimethyl-4-(4-methoxycarbonyl-3,3-dimethylbutyl)thiophene

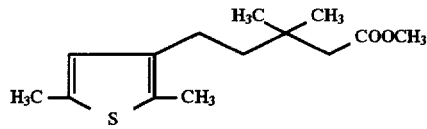

This product was prepared analogously to the preparation of the product forming the subject of paragraph B) Step 3, using 2,5-dimethylthiophene as starting material.

Step 2: 2,5-dimethyl-3-(3-oxo-3-phenylpropyl)-4-(4-methoxycarbonyl-3,3-dimethylbutyl)thiophene

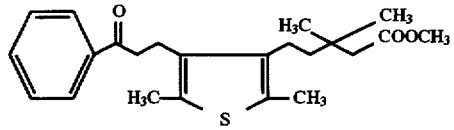

8.36 g (0.0328 mol) of 2,5-dimethyl-4-(4-methoxycarbonyl-3,3-dimethylbutyl)thiophene, 7 g (0.0328 mol) of 3-bromopropionylbenzene and 120 ml of dichloromethane are placed in a 250 ml three-necked flask fitted with a magnetic stirrer, a thermometer and a dropping funnel. While maintaining the temperature below 5° C., 10.7 g (0.0410 mol) of SnCl₄ are poured in. After 12 hours at room temperature, the mixture is hydrolysed with a mixture of water/ice/concentrated HCl (150 g/150 g/50 ml). The organic phase is washed with dilute HCl, H₂O, and then dried over MgSO₄, rendered colourless with carbon black and concentrated. The residue is chromatographed on silica (eluant: CH₂Cl₂). The relevant fractions are concentrated yielding 5.85 g of the expected ester in the form of a colourless oil, yield: 46%.

Step 3: Title product 6.4 g (0.0166 mol) of 2,5-dimethyl-3-(3-oxo-3-phenylpropyl)-4-(4-methoxycarbonyl-3,3-dimethylbutyl)thiophene and 100 ml of triethylene glycol are placed in a 250 ml three-necked flask fitted with a mechanical stirrer, a condenser and a thermometer. The temperature is brought to 60° C., 1.86 g (0.0580 mol) of 80% hydrazine hydrate are added to the reaction mixture and then, at 90° C., 2.84 g (0.050 mol) of potassium hydroxide are added. The reaction mixture is then brought to a vigorous reflux and, after the removal of water by distillation, the temperature is maintained at 210° C. for 45 minutes. After cooling, the mixture is hydrolysed with a mixture of water/ice/concentrated HCl (200 g/100 g/17 ml) and then extracted with ether. The combined organic phases are washed with dilute HCl, H₂O, and then dried over MgSO₄, rendered colourless with carbon black and concentrated to yield 4.5 g of 2,5-dimethyl-3-(3-phenylpropyl)-4-(4-carboxy-3,3-dimethylbutyl)thiophene in the form of a pale yellow oil, yield: 75%.

II. Synthesis of the compounds of formula I

EXAMPLE 1

2,3-dimethyl-4-(3-p-methylphenylpropyl)-5-(5-morpholino-3,3-dimethylpentyl)thiophene

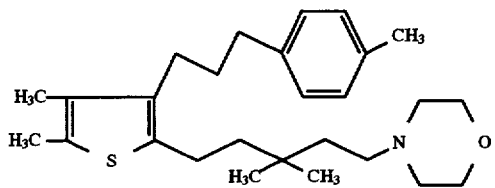

and its hydrochloride.

Step 1: 2,3-dimethyl-4-(3-p-methylphenylpropyl)-5-(4-morpholinocarbonyl-3,3-dimethylbutyl)thiophene

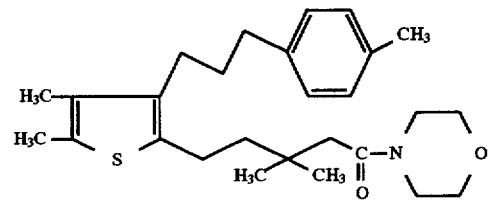

2 g (0.0157 mol) of oxalyl chloride dissolved in 10 ml of CHCl₃ are placed in a 100 ml single-necked flask. After having brought the mixture to 0° C. with an ice bath, 3.9 g (0.0105 mol) of 2,3-dimethyl-4-(3-p-methylphenylpropyl)-5-(4-carboxy-3,3-dimethylbutyl)thiophene (see above, paragraph B of the synthesis of the starting materials) are added. The reaction mixture is then stirred at room temperature and subsequently at 50° C. until the evolution of gas has ceased.

The solvent is distilled off at a temperature below 50° C. The acid chloride prepared above dissolved in 60 ml of ether, and 1.82 g (0.021 mol) of morpholine dissolved in 60 ml of ether, are simultaneously poured into a 500 ml three-necked flask while stirring. The morpholinium hydrochloride precipitates instantaneously. After one hour's stirring, the solid is removed by filtration. The filtrate is washed with water, dried over MgSO₄, rendered colourless with carbon black and concentrated to dryness. The crude product obtained is purified by chromatography on silica (eluant: CH₂Cl₂/CH₃COOC₂H₅-95/5, then CH₂Cl₂/CH₃OH-98/2). 3.31 g of 2,3-dimethyl-4-3-p-methylphenylpropyl)-5-(4-morpholinocarbonyl-3,3-dimethylbutyl)thiophene are obtained in the form of a colourless oil, yield: 72%.

Step 2: Title product 0.45 g (0.0119 mol) of LiAlH₄ are suspended in 12 ml of ethyl ether in a 50 ml three-necked flask fitted with a magnetic stirrer and a condenser, under a nitrogen-flow. 2.56 g (0.0058 mol) of the amide prepared in Step 1 above dissolved in 12 ml of ether are added in the course of approximately 30 minutes. The reaction is exothermic. The reaction mixture is maintained at reflux for 1 hour, then cooled to 20° C. and hydrolysed with H₂O (0.45 ml), 4N NaOH (0.45 ml) and H₂O (0.9 ml). The solid is removed by filtration and washed with ether. The organic phases are washed with water, dried over MgSO₄ and rendered colourless with carbon black.

The hydrochloride of the title product is precipitated by the addition of an equivalent of HCl dissolved in ether, suctioned off and dried in vacuo. 1.64 g of 2,3-dimethyl-4-(3-p-methyl-phenylpropyl)-5-(5-morpholino-3,3-dimethylpentyl)thiophene hydrochloride are obtained in the form of a white crystalline solid, m.p.: 138° C., yield: 61%.

EXAMPLES 2–9

By proceeding in accordance with the method of operation described in Example 1, starting from appropriate acids the preparation of which has been described in paragraph I, the compounds forming the subject of the following Examples were prepared:

2) 2,5-dimethyl-3-(3-phenylpropyl)-4-(5-morpholino-3,3-dimethylpentyl)thiophene and its hydrochloride melting at 167° C.

3) 2,5-dimethyl-3-(3-phenylpropyl)-4-{5-[4-(2,3,4-trimethoxybenzyl)piperazin-1-yl]-3,3-dimethylpentyl}thiophene, and its dihydrochloride melting at 165° C. (purity: 98%).

4) 2,3-dimethyl-4-(3-p-methylphenylpropyl)-5-{5-[4-(2,3,4-trimethoxybenzyl)piperazin-1-yl]-3,3-dimethylpentyl}thiophene, and its dihydrochloride melting at 150° C. (purity: 99%).

5) 2-methyl-3-{5-[4-(2,3,4-trimethoxybenzyl)-piperazin-1-yl]-3,3-dimethylpentyl}-5-(3-p-methylphenylpropyl)thiophene, and its dihydrochloride melting at 200° C. (purity: 96%).

6) 2-methyl-4-(5-morpholino-3,3-dimethylpentyl)-5-(3-p-methylphenylpropyl)thiophene, and its hydrochloride melting at 164° C. (purity: 98%).

7) 2-methyl-4-{5-[4-(2,3,4-trimethoxybenzyl)piperazin-1-yl]-3,3-dimethylpentyl}-5-(3-p-methylphenylpropyl}thiophene and its dihydrochloride melting at 180° C. (purity: 99%).

8) 2-methyl-3-(3-p-methylphenylpropyl)-5-{5-[4-(2,3,4-trimethoxybenzyl)piperazin-1-yl]-3,3-dimethylpentyl}thiophene, and its dihydrochloride melting at 200° C. (purity: 99%).

9) 2-methyl-4-(3-p-methylphenylpropyl)-5-{5-[4-(2,3,4-trimethoxybenzyl)piperazin-1-yl]-3,3- dimethylpentyl}thiophene, and its dihydrochloride melting at 170° C. (purity: 98%).

EXAMPLE 10

Pharmacological Study

The compounds of the present invention exhibit valuable pharmacological properties, especially in respect of bone metabolism.

In the normal state, bone remodelling allows the anatomical and structural integrity of the skeleton to be assured. It occurs in cycles and depends on two main types of cell population, the osteoclasts and the osteoblasts. The osteoclasts, after activation, ensure resorption of old bone by acidification and subsequent enzymatic digestion leaving room, in a successive phase, for the osteoblasts to form new osteoid tissue which will then be calcified.

Those two metabolic phases—resorption and formation—are closely coupled with one another in the physiological state. In a pathological situation, an imbalance between those two phases may be produced with, in particular, a resorption hyperactivity, which brings about excessive bone loss that is inadequately compensated by the neoformation phase. This is especially the case with post-menopausal osteoporosis.

The activity of the compounds described has been demonstrated in particular in a test carried out on the isolated tissue of mice skull-caps in which bone resorption is stimulated by retinoic acid. The method used is directly inspired by the technique described by J. J. REYNOLDS et al Calc. Tiss. Tes. 4, 339–49 (1970).

In that situation of hyper-resorption, the compounds used at molar concentrations of from $10^{-6}$ to $10^{-5}$ brought about variations ranging from −3 to −45%. By way of illustration, the compounds of Examples 2 and 3, particularly representative of the invention, gave the following results:

| Compounds | Molar concentration | % variation |
|---|---|---|
| Example 2 | $10^{-6}$ | −3% |
|  | $5 \times 10^{-6}$ | −13% |
|  | $10^{-5}$ | −17% |
| Example 3 | $10^{-6}$ | −7% |
|  | $5 \times 10^{-6}$ | −31% |
|  | $10^{-5}$ | −42% |

Those compounds thus exhibit valuable anti-resorbent properties allowing their therapeutic use in pathologies characterized by a bone loss especially when that is as a result of excess resorption.

We claim:

1. A compound selected from:

thiophene compounds of formula I:

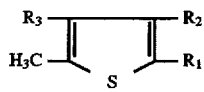

(I)

wherein:

one of $R_1$, $R_2$ and $R_3$ represents:

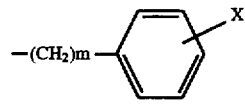

wherein:

m represents an integer of 2 to 6 inclusive and

X is selected from the group consisting of hydrogen, alkyl and alkoxy each having 1 to 5 carbon atoms inclusive in straight or branched chain, and dialkylamino in which each alkyl contains 1 to 5 carbon atoms inclusive, one of $R_1$, $R_2$ and $R_3$ represents:

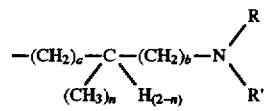

wherein:

n is selected from the group consisting of 0, 1 and 2;

a is selected from the group consisting of 2 and 3 and b is selected form the group consisting of 1 and 2, such that a+b=4, and R and R', which are identical or different, are each selected from the group consisting of hydrogen and alkyl having 1 to 5 carbon atoms inclusive in straight or branched chain, or R and R' form, together with the nitrogen to which they are bonded, a five-membered or six-membered heterocyclic group optionally containing an oxygen or a second nitrogen, which nitrogen may itself be substituted by alkyl containing 1 to 5 carbon atoms inclusive in straight or branched chain or by arylalkyl in which the alkyl group contains 1 to 5 carbon atoms and the aryl group is optionally mono- or poly-substituted by halogen or by alkyl, or alkoxy each having 1 to 5 carbon atoms inclusive, and one of $R_1$, $R_2$ and $R_3$ represents hydrogen or methyl, and the physiologically-tolerable salts thereof with an acid.

2. A compound of claim 1 which is selected from 2,3-dimethyl-4-(3-p-methylphenylpropyl)-5-(5-morpholino-3, 3-dimethyl pentyl)thiophene, and its hydrochloride.

3. A method for treating a living animal body afflicted with a pathology characterized by a loss of bone tissue, comprising the step of administering to the said living animal body an amount of a compound of claim 1 which is effective for the alleviation of said pathology.

4. A pharmaceutical composition useful in treating bone tissue loss, comprising as active ingredient a compound of claim 1 mixed with or associated with one or more pharmaceutical excipients.

* * * * *

UNITED STATES PATENT AND TRADEMARK OFFICE
CERTIFICATE OF CORRECTION

PATENT NO. : 5,703,074
DATED : Dec. 30, 1997
INVENTOR(S) : M. Wlerzbicki, F. Sauveur, M. Boussard, J. Bonnet, M. Sabatini It is certified that error appears in the above-identified patent and that said Letters Patent is hereby corrected as shown below:

Column 2, line 43: In the formula, the bottom far right "R" should read -- R' --.

Column 3, line 1: "formula III" should read -- formula II --.

Column 3, line 62: "distillation/n vacuo." should read -- distillation in vacuo. --.

Column 7, line 51: "$CH_2C_{12}$" should read -- $CH_2Cl_2$ --.

Column 12, line 11: Insery a -- , -- after "alkyl" and also after "alkoxy". Page 1 of Preliminary Column 12, line 41: Insert a -- , -- after the word "alkoxy".

Signed and Sealed this

Seventeenth Day of March, 1998

Attest:

BRUCE LEHMAN

*Attesting Officer*     *Commissioner of Patents and Trademarks*